US009504451B2

(12) United States Patent
Tamano

(10) Patent No.: US 9,504,451 B2
(45) Date of Patent: Nov. 29, 2016

(54) ULTRASOUND DIAGNOSTIC APPARATUS AND SHEAR-ELASTICITY MEASUREMENT METHOD THEREFOR

(75) Inventor: Satoshi Tamano, Kashiwa (JP)

(73) Assignee: HITACHI MEDICAL CORPORATION, Tokyo (JP)

(*) Notice: Subject to any disclaimer, the term of this patent is extended or adjusted under 35 U.S.C. 154(b) by 134 days.

(21) Appl. No.: 14/130,561

(22) PCT Filed: May 23, 2012

(86) PCT No.: PCT/JP2012/063119
§ 371 (c)(1),
(2), (4) Date: Jan. 2, 2014

(87) PCT Pub. No.: WO2013/015001
PCT Pub. Date: Jan. 31, 2013

(65) Prior Publication Data
US 2014/0148698 A1    May 29, 2014

(30) Foreign Application Priority Data
Jul. 28, 2011    (JP) .................. 2011-165662

(51) Int. Cl.
A61B 8/00    (2006.01)
A61B 8/08    (2006.01)
A61B 5/01    (2006.01)
G01S 7/52    (2006.01)

(52) U.S. Cl.
CPC ............... *A61B 8/546* (2013.01); *A61B 5/01* (2013.01); *A61B 8/085* (2013.01); *A61B 8/461* (2013.01); *A61B 8/485* (2013.01); *A61B 8/5223* (2013.01); *G01S 7/52036* (2013.01); *G01S 7/52042* (2013.01); *G01S 7/52074* (2013.01)

(58) Field of Classification Search
CPC ...................................................... A61B 8/485
See application file for complete search history.

(56) References Cited

U.S. PATENT DOCUMENTS 6,951,544 B2    10/2005    Trahey et al.
2004/0034304 A1    2/2004    Sumi
(Continued)

FOREIGN PATENT DOCUMENTS

JP    A-2000-5165    1/2000
JP    A-2003-210460    7/2003
(Continued)

OTHER PUBLICATIONS

International Search Report issued in International Patent Application No. PCT/JP2012/063119 dated Aug. 21, 2012 (w/translation).

*Primary Examiner* — Rochelle Turchen
(74) *Attorney, Agent, or Firm* — Oliff PLC

(57) ABSTRACT

An inventive ultrasound diagnostic device is provided, which can display information on the temperature rise in a biological object under ultrasound radiation for measurement of a shear elasticity of a biological tissue of interest, thereby drawing attention of an examiner of the device and enabling him to retain the temperature rise within a predetermined safe range while performing the shear elasticity measurement. The device is adapted to measure the shear elasticity of a tissue by ultrasonic waves emitted from a probe. The device has a calculation unit configured to calculate a rise in temperature of the biological tissue irradiated with a focused ultrasonic (US) beam, and a display unit configured to display the temperature information obtained.

7 Claims, 7 Drawing Sheets

(56) References Cited

U.S. PATENT DOCUMENTS

2006/0184020 A1* 8/2006 Sumi .............................. 600/437
2010/0191113 A1   7/2010 Hazard et al.
2010/0280373 A1  11/2010 Fan et al.
2012/0136250 A1*  5/2012 Tabaru et al. ................. 600/438

FOREIGN PATENT DOCUMENTS

| JP | A-2008-67856 | 3/2008 |
| JP | A-2010-172699 | 8/2010 |
| JP | A-2010-259806 | 11/2010 |
| WO | WO 2011/027644 A1 | 3/2011 |

* cited by examiner

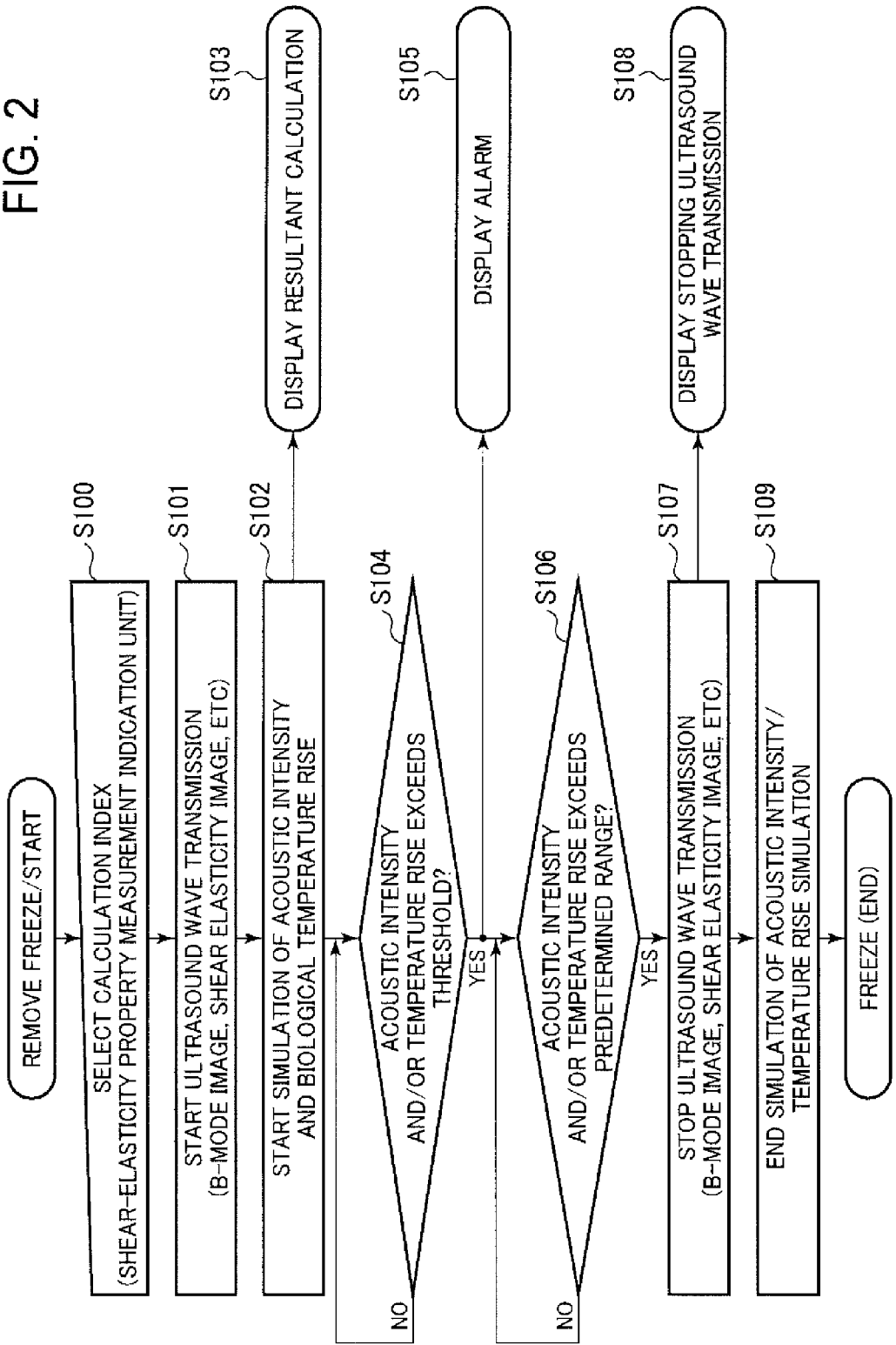

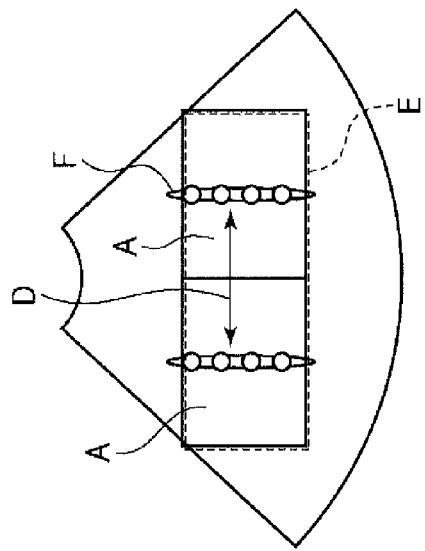
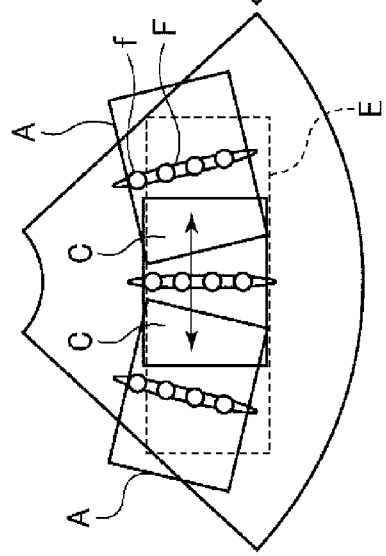
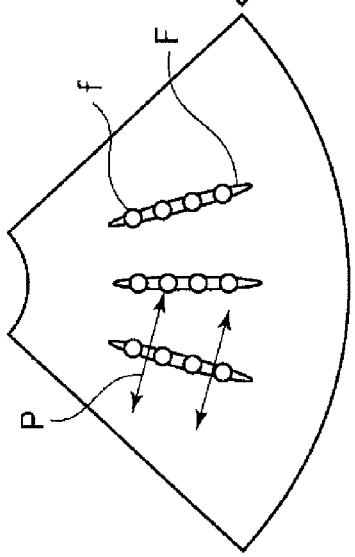

FIG. 5
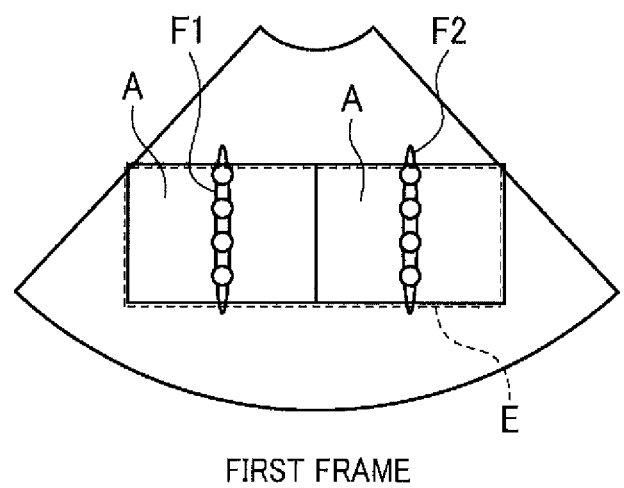
FIRST FRAME
↕ SWITCHING
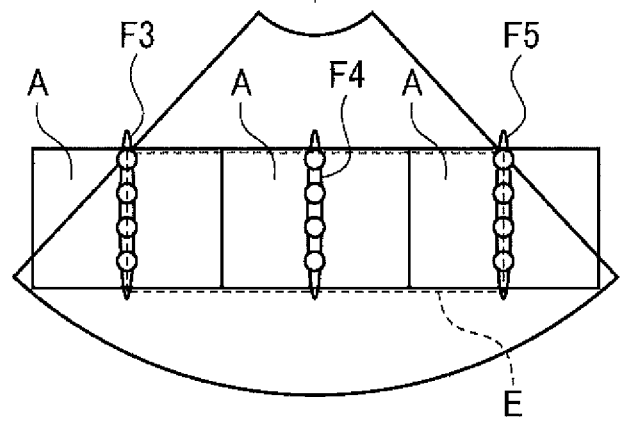
SECOND FRAME

ULTRASOUND DIAGNOSTIC APPARATUS AND SHEAR-ELASTICITY MEASUREMENT METHOD THEREFOR

TECHNICAL FIELD

This invention relates to an ultrasound diagnostic device and a method for measuring the shear-elasticity of a biological tissue, particularly capable of reducing temperature rise in the biological domain irradiated with ultrasound wave while safely measuring such shear-elasticity.

BACKGROUND ART

It has been well known in the art that a biological tissue afflicted by a tumor (for example, breast cancer and prostatic cancer) significantly hardens as the tumor grows as compared with healthy tissues. It is also known that in a region afflicted by such tumor a transverse ultrasound has an increased speed. Thus, there has been proposed a method of discerning a tumor-afflicted biological region by transmitting an ultrasound wave through the region and measuring the ultrasound shear rate of the domain. (See for example, Patent Document 1 listed below.)

PRIOR ART DOCUMENTS

Patent Document

Patent Document 1: U.S. Pat. No. 6,951,544

SUMMARY OF INVENTION

Objects to be Achieved by the Invention

In order to induce a shear displacement in a targeted biological tissue (for example, having a tumor) by a transverse ultrasound energy, it is necessary to irradiate its ambient region with an energetic ultrasound wave. However, the biological tissue will be then overheated and necrotized if the ultrasound energy deposited to the tissue is too high, since the ultrasonic energy is converted to heat in the biological tissue.

In view of the prior art problems mentioned above, it is an object of the present invention to provide an ultrasound diagnostic apparatus configured to irradiate a biological tissue of interest with ultrasound wave to safely measure the shear elasticity of the tissue without overheating the tissue during the measurement, and a method of measuring the shear-elasticity of tissue.

Means for Carrying Out the Invention

An inventive ultrasound diagnostic device is a device configured to measure a shear elasticity of an object by an ultrasound wave emitted from a probe. The device has a calculation unit configured to calculate a rise in temperature in a focusing region where the ultrasound wave is focused and a display unit configured to display information on the temperature rise.

Thus, the apparatus can invite examiner's attention to the temperature rise of a tissue by displaying information on the temperature rise, thereby retaining the physiological object within a predetermined safe temperature range during the shear elasticity measurement. The probe can irradiate a plurality of focusing regions with ultrasound wave, while the calculation unit can calculate the shear elasticity.

An inventive method comprises measuring a shear elasticity of an object exposed to the ultrasound wave emitted from the probe by calculating the rise in temperature in the focusing region, and displaying information related to the temperature rise.

In this arrangement, the apparatus can invite attention of the examiner by displaying such temperature information, so that the rise in temperature of a physiological object can be suppressed within a predetermined range for a safe measurement of the shear elasticity of the biological tissue under ultrasound irradiation.

Results of the Invention

According to the present invention, the apparatus can invite examiner's attention by displaying information on the temperature rise and allows a safe shear elasticity measurement of the biological tissue irradiated with an ultrasound wave while suppressing the temperature rise of the tissue within a predetermined permissible range.

BRIEF DESCRIPTION OF THE DRAWINGS

FIG. 2 is a flowchart illustrating the operation of the ultrasound diagnostic device in accordance with the first embodiment.

FIG. 4(a) is a schematic diagram showing the direction of propagation of a transverse ultrasound wave when an ultrasound wave is irradiated to a fan-shape tissue area.

FIG. 4(b) is a schematic diagram showing an area in which transverse ultrasound waves propagate when an ultrasound wave is irradiated to a fan-shape tissue domain.

FIG. 4(c) is a schematic diagram showing how overlapping of propagation areas can be reduced by providing a plurality of focusing regions F in substantially parallel to each other.

FIG. 5 is a schematic diagram showing how positions of focusing region are changed by imaging frames in shear elasticity measurement.

BEST MODE FOR CARRYING OUT THE INVENTION

First Embodiment

Figure 1:
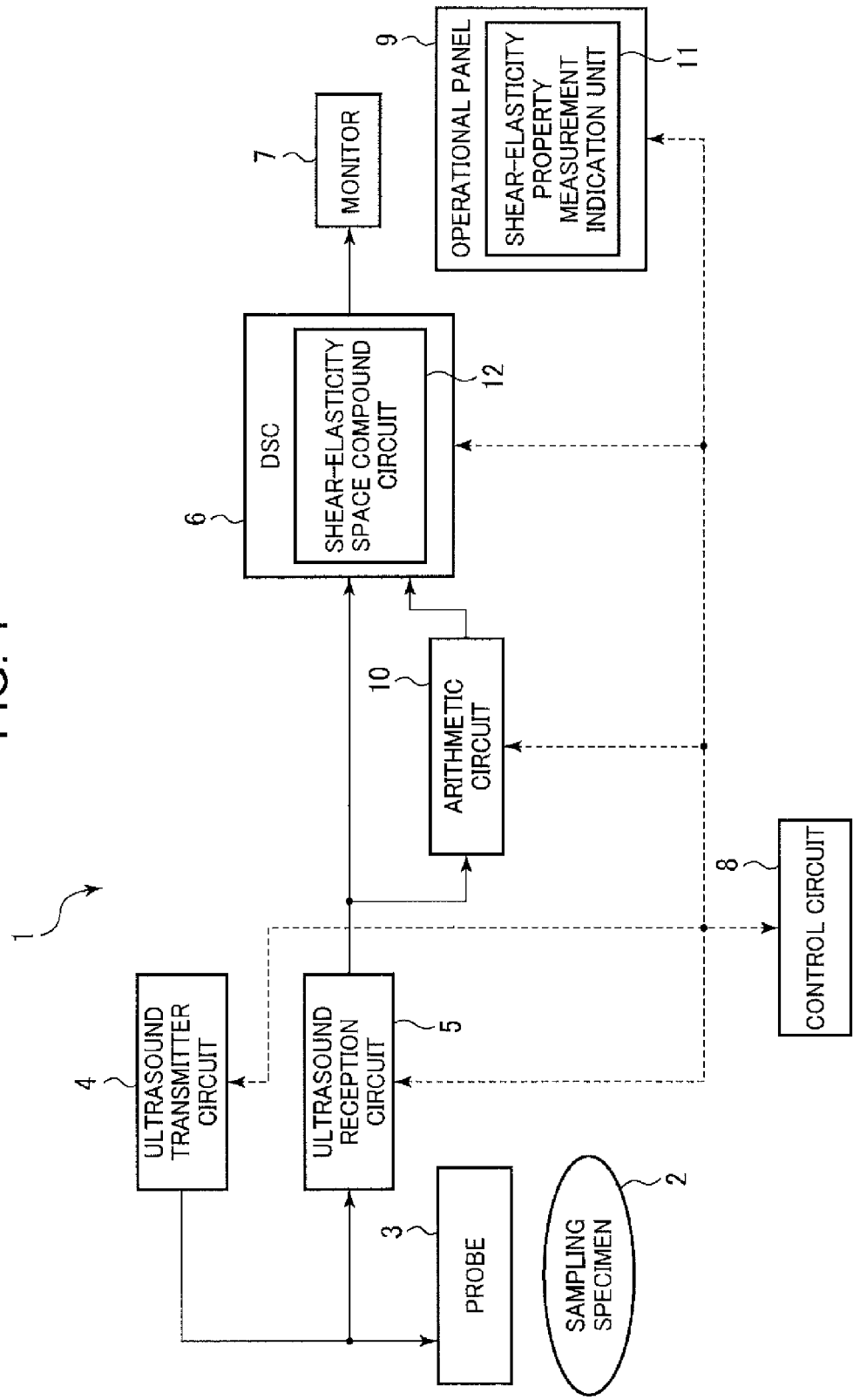
FIG. 1 is a schematic diagram of an ultrasound diagnostic device in accordance with a first embodiment of the invention.

The ultrasound diagnostic device in accordance with a first embodiment of the invention will now be described in detail with reference to the accompanying drawings. FIG. 1 briefly shows a first mode of the inventive ultrasound diagnostic device.

This ultrasound diagnostic device 1 has a probe 3, an ultrasound transmitter circuit 4, an ultrasound receiving circuit 5, a digital scanning converter (DSC) 6, a monitor (display unit) 7, a control circuit (control unit) 8, an operation panel 9, and a calculation circuit (calculation unit) 10. The DSC 6 has a shear-elasticity space compound circuit 12. The operation panel 9 has a shear-elasticity property measurement-indication unit 11.

The probe 3 has an ultrasound oscillator unit which comprises a plurality of oscillators configured to emit ultrasound waves to an object (a sampling specimen) 2. The probe 3 can be a linear array of probes each equipped with a reed shape oscillator, or a 2-dimensional array of probes. The ultrasound transmitter circuit 4 generates an ultrasound transmission signal to the ultrasonic oscillator unit of the probe 3, under the control of the control circuit 8. The ultrasound receiving circuit 5 receives signals from the ultrasonic oscillator unit of the probe 3 and performs phase-matching of the ultrasound signals under the phase matching and shifting control of the control circuit 8. Upon receipt of a phase-matching signal from the ultrasound receiving circuit 5, the digital scanning converter (DSC) 6 displays an ultrasound image on the monitor 7. For example, the digital scanning converter (DSC) 6 constructs such ultrasound images as B-mode and M-mode images, a Doppler image, and a blood flow image and display them on the monitor 7. The digital scanning converter (DSC) 6 constructs a shear elasticity image based on the shear elasticity calculation made by the calculation circuit 10, and displays the image on the monitor 7. The monitor (display unit) 7 displays different types of information including such ultrasound image.

The control circuit 8 controls various components of the ultrasound diagnostic device 1. In addition to a CPU, the control circuit 8 may include such components as a DSP, an FPGA, or an RISC. The operation panel 9 functions as a user interface configured to input a control data to operate the ultrasound diagnostic device 1 Utilizing the output signal received from the ultrasound receiving circuit 5, the calculation circuit (calculation unit) 10 calculates the shear elasticity of a predetermined domain of the object 2. The result of the shear elasticity calculation is converted into a shear elasticity image by the digital scanning converter (DSC) 6 and displayed on the monitor 7. The result of the shear elasticity calculation may be superimposed on the image, or shown adjacent the image. The result may be solely shown on the display.

The shear-elasticity property measurement-indication unit 11 sets up different conditions for the measurement of the shear elasticity property. The shear-elasticity property measurement-indication unit 11 is provided with a touch panel, a button, or a GUI. Although the shear-elasticity property measurement-indication unit 11 of this embodiment is implemented as a part of the operation panel 9, the unit 11 may be provided as an independent unit. A shear-elasticity space compound circuit 12 superimposes a plurality of ultrasound shear elasticity images on the monitor 7.

In FIG. 1, solid lines indicate flows of ultrasound data, and broken lines indicate flows of control signals.

The calculation circuit 10 calculates a rise in temperature (referred to as temperature rise) of a focusing region of the object 2 where an irradiating beam is focused. The monitor 7 displays information on the temperature rise, including thermal index (TI), mechanical index (MI), thermal dose (TD), and time-to-threshold (TT).

The thermal index is an index indicative of thermal effect of irradiation, indicating possible temperature rise in the tissue caused by the current US beam. TI is calculated by the following formula.

$$TI = Wo/W\text{deg} \quad (1)$$

where

Wo is the radiative power (in Watt) of the beam radiated from the probe of the ultrasound diagnostic device, and Wdeg is the power (in Watt) required to raise the temperature of a given biological tissue by 1° C.

(Quoted from WFUMB, WFUMB Symposium on Safety and Standardization in Medical Ultrasound, Synopsis, Ultrasound Med Boil 18, 1992, PP. 733-737 (non-patent document)) Mechanical index (MI) indicates the negative sound pressure of an ultrasound wave of a given frequency in terms of the negative sound pressure of 1 MHz, the conversion being based on the fact that the energy liberated from a collapsing bubble, when compared under the same negative sound pressure, is inversely compounding rational to the frequency. MI is useful in comparing expected mechanical and chemical effects of ultrasounds of different frequencies. MI is calculated by the following formula (2).

$$MI = Pr \cdot \alpha(Zsp)/\sqrt{(fc)} \quad (2)$$

where fc is the central frequency (in MHz) of a pulsed wave, and $Pr \cdot \alpha(Zsp)$ is the negative sound pressure (in MPa) of an ultrasound wave evaluated at the point Zsp where the integral of the intensity of the pulsed wave is maximum, taking account of the biological dissipation of the wave, (References: Robert E. APFEL, "Possibility of Microcavitation from Diagnostic Ultrasound", IEEE Trans. UFFC 33(2) (1986) pp. 139-142(non-patent document); Christy K, HOLLAND and Robert E. APFEL, "An Improved Theory for the Prediction of Microcavitation Thresholds", IEEE Trans. UFFC 36(2) (1989) pp 204-208 (non-patent document); The Thermal Dose Index, Marvin C. Ziskin, J. Ultrasound Med. 2010; 29:1475-1479 (non-patent document); and Lubbers, J. Hekkenberg, R. T., and Bezemer, R. A. (2003). "Time to threshold, a safety parameter for heating by diagnostic ultrasound", Ultrasound Med. Biol. 29, 755-764 (non-patent document))

The ultrasound diagnostic device 1 in accordance with one embodiment of the invention is adapted to suppress temperature rise in a physiological object within a predetermined threshold and/or within a predetermined safe range while irradiating an ultrasound wave to the object, so that the shear elasticity of a biological tissue of interest within the object can be safely measured. The Guidelines provided by a global academic organization of medical ultrasound treatment, World Federation for Ultrasound in Medicine and Biology (WFUMB) is herein incorporated by reference as the predetermined range of temperature rise. Regarding thermal and non-thermal effects of ultrasound irradiation, it is stated in the Guidelines that (1) There will be no influence if temperature rise does not exceed 1.5° C.;
(2) There can be an influence on an embryo and an infant if temperature rise exceeds 4° C. for more than 5 minutes;
(3) Effects depend on the irradiation period of time;
(4) Notification of the intensity of the ultrasound wave to the examiner is required if the apparatus causes a temperature rise of more than 1.5° C.

The present embodiment fully complies with the WFUMB Guidelines, and the calculation circuit 10 performs real time calculation of various ultrasound transmission intensities associated with TI, MI, TT, and TD, along with other indices such as biological temperature rise index. The monitor 7 displays different ultrasound transmission intensities and biological temperature rise indices in real time as they are calculated by the calculation circuit 10. The control circuit 8 may be configured to issue an alarm to the examiner via the monitor 7 when the temperature rise of the object 2 is likely to reach or exceed the threshold and/or the predetermined range. In those cases where the temperature rise of the object 2 is likely to reach or exceed the threshold and/or range, the control circuit 8 may control the ultrasound transmitter circuit 4 to generate an ultrasound signal for suppressing the temperature rise of the object 2 within the predetermined threshold and/or within the predetermined range. Further, the control circuit 8 may control the ultrasound transmitter circuit 4 so as to stop the ultrasound transmission signal (hereinafter referred to as US transmission signal) when the temperature rise in the object 2 is likely to reach or exceed the threshold and/or the predetermined range.

As described above, the inventive ultrasound diagnostic device comprises a calculation unit (calculation circuit 10) configured to calculate temperature rise in a focusing region of the object 2 under ultrasound wave emitted from the probe 3 and a display unit (monitor 7) configured to display the calculated data indicative of the temperature rise. The inventive method of measuring the shear elasticity of the object 2 measures the shear elasticity of the object 2 irradiated by an ultrasound wave emitted from a probe and calculates the temperature rise in the focusing region due to deposition of ultrasound energy, and displays relevant information regarding the temperature. By displaying such temperature information, this method makes it possible to invite examiner's attention and to suppress the temperature rise in the physiological object within a predetermined range while safely measuring the shear elasticity of a biological tissue under ultrasound wave.

The calculation circuit (calculation unit) 10 calculates temperature rise using at least one of such indices as thermal index, mechanical index, thermal dose, and time-to-threshold, and displays the temperature rise on the monitor 7. In this configuration, it is possible, through a real time calculation of, for example, the ultrasound wave intensity transmitted and biological temperature rise index, to display that the temperature rise may reach or exceed the predetermined threshold and/or the range.

In the case where the temperature rise in the physiological object is likely to reach or exceed the predetermined threshold and/or predetermined range, the ultrasound transmitter unit (ultrasound wave transmitter circuit) 4 generates an ultrasound wave transmission signal to suppress the temperature rise in the physiological object within the predetermined threshold and/or within the predetermined range. Alternatively, the ultrasound transmitter circuit 4 may stop generating the ultrasound wave transmission signal.

Next, operations of the ultrasound diagnostic device 1 of the present embodiment will now be described in detail below. FIG. 2 is a flowchart illustrating operations of the ultrasound diagnostic device 1.

In Step S100, at least one of the indices TI, MI, TT, and TD is selected utilizing the shear-elasticity property measurement-indication unit 11. However, more than one index may be selected simultaneously. The ultrasound diagnostic device 1 starts transmission of an ultrasound wave (Step S101). Then, a US beam is emitted from the probe 3 onto the object 2 in accordance with the ultrasound transmission signal generated by the ultrasound transmitter circuit 4.

Using a simulation function, the calculation circuit 10 performs real time calculation of US transmission intensities (sound intensities) associated with selected indices along with other indices such as biological temperature rise index (step S102). When the calculation circuit 10 is calculating an ordinary ultrasound image (B-mode image for example), the calculation circuit 10 may stop calculation of the shear elasticity. When the operational mode of the calculation circuit 10 is to be switched between an ordinary ultrasound image capturing mode and an shear elasticity image capturing mode, the calculation circuit 10 may be switched to a mode for calculating indices associated with the shear elasticity and temperature rise. In other words, in measuring the shear elasticity of the object 2 using an ultrasound wave emitted from the probe 3, the calculation circuit 10 may assume a mode adapted to calculate both indices associated with the shear elasticity and the temperature rise. Consequently, unnecessary shear elasticity measurement can be omitted.

In the ultrasound diagnostic device of the present invention, the calculation circuit (calculation unit) 10 is switched to the temperature rise calculation mode when measuring the shear elasticity of the object 2 under irradiating of the ultrasonic wave from the probe 3. In this calculation mode, unnecessary shear elasticity measurement of the, which is otherwise involved in the calculation of the shear elasticity, is omitted.

The calculated index is displayed on the monitor 7 (Step S103). The control circuit 8 determines whether or not the calculated ultrasound transmission intensity (acoustic intensity) and the biological temperature rise index exceed respective preset thresholds (Step S104). In the case where the calculated temperature rise in the object 2 is likely to reach a predetermined range, the control circuit 8 displays an alarming signal as a warning to the examiner.

The control circuit 8 determines if the calculated ultrasound transmission intensity (acoustic intensity) and the biological temperature rise index exceed respective predetermined ranges (Step S106). The predetermined range(s) may follow the WFUMB guidelines. If the calculated result(s) exceed(s) the predetermined range(s), the control circuit 8 issues an alarm to the examiner via an alarming signal displayed on the monitor 7, and stops transmitting the ultrasound (Step S107). Then the monitor 7 displays termination of the ultrasound transmission signal (Step S108).

After acquisition of ordinary ultrasound images and shear elasticity images, the calculation circuit 10 ends the ultrasound transmission intensity (acoustic intensity) simulation and the biological temperature rise index simulation (Step S109).

Using the ultrasound diagnostic device in accordance with the present embodiment of the invention, the shear elasticity of a given biological tissue can be safely measured through appropriate irradiation of an ultrasound wave to the object 2 while calculating indices associated with the temperature rise in the object 2 and displaying them on the monitor 7. By stopping the transmission of the ultrasound wave when the indices are likely to exceed the predetermined thresholds and/or the predetermined ranges, shear elasticity of the biological tissue can be safely measured through appropriate irradiation of an ultrasound wave thereto. It is noted that, the indices associated with the US transmission intensity and in-biological tissue temperature rise are not limited to TI, MI, TT, and TD. Other indices such as ISPTA.3 may be used equally well.

Second Embodiment

An ultrasound diagnostic device in accordance with a second embodiment of the invention will now be described in detail with reference to the accompanying drawings. Other structural features of the second embodiment are similar to those of the first embodiment unless otherwise stated. FIG. 3 briefly illustrates how ultrasound wave is irradiated by the ultrasound diagnostic device in accordance with this embodiment.

Figure 3A:
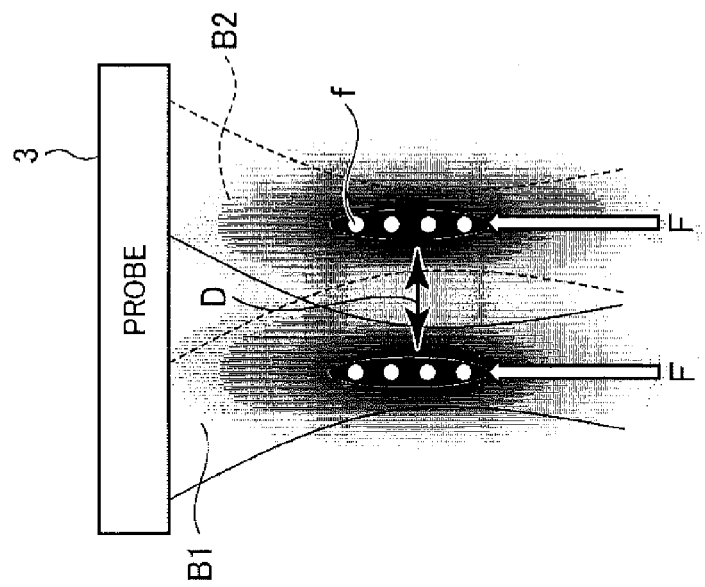
FIG. 3 is a schematic diagram illustrating how a beam or beams of ultrasound wave (hereinafter referred to as US beam(s)) is(are) irradiated by the ultrasound diagnostic device in accordance with a second embodiment of the invention.

FIG. 3(a) shows a single beam B1 of ultrasound wave irradiating the object 2 in one direction to cause a biological shear stress therein. In order to generate transverse waves at different depths in a biological region for the purpose of causing a shear stress in that region, such US beam B1 is focused onto multiple focusing points f at different depths in sequence. A depth-wise region that includes those multiple focusing points f is referred to as focusing region F. When an ultrasound wave beam B1 is irradiated to a biological tissue in one direction as shown in FIG. 3(a), the irradiation is localized and so is the temperature rise, so that the temperature rise can reach a predetermined threshold or exceed a predetermined range in a short period of time. Therefore, in order to measure the shear elasticity safely, it is necessary to shorten the measurement time, which may prevent a satisfactory examination.

Figure 3B:
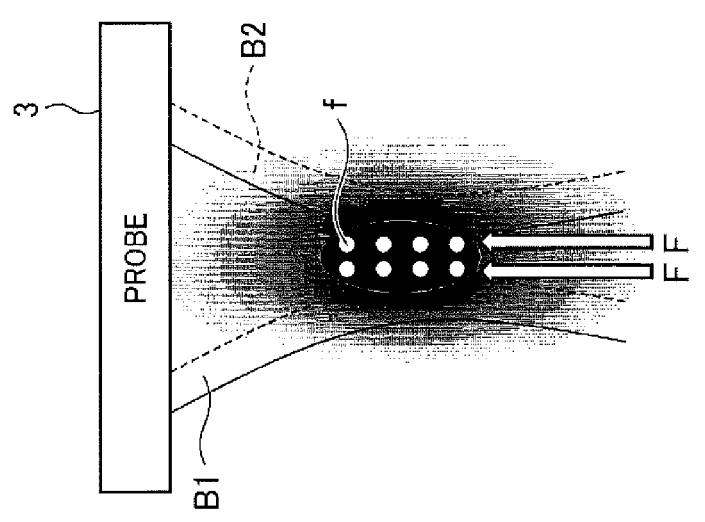
Figure 3C:
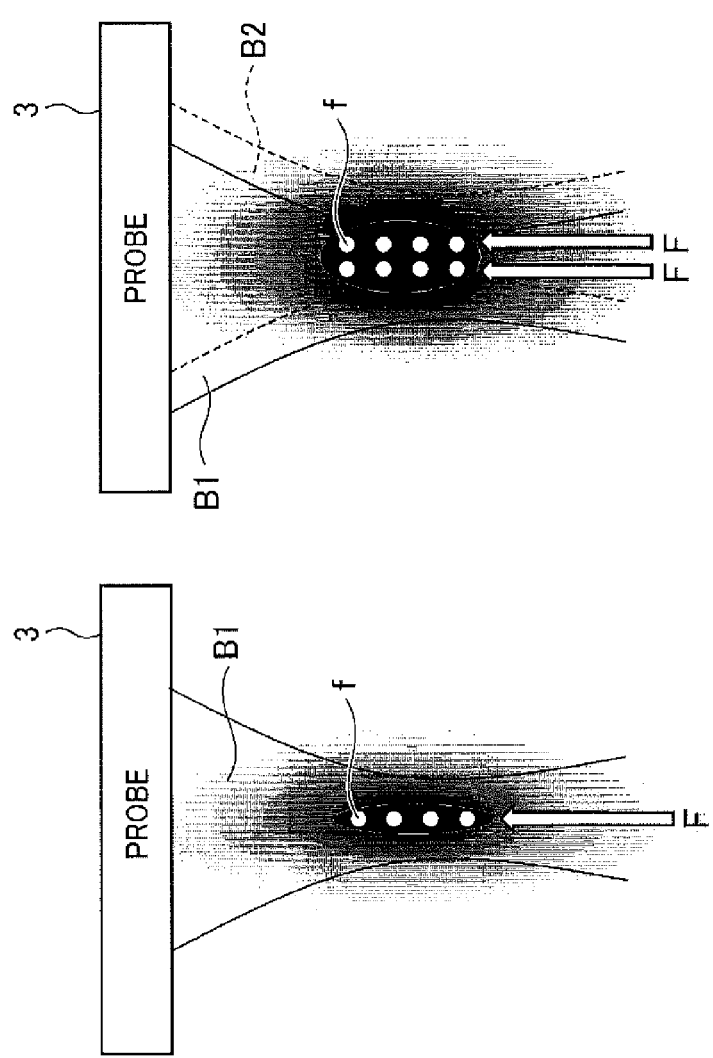

In the present embodiment, a plurality of US beams B1 and B2 for example are irradiated onto a plurality of focusing regions F, as shown in FIGS. 3(b) and 3(c). It is noted that when a plurality of focusing regions F overlap or when a plurality of propagation areas of the transverse ultrasound wave overlap as shown in FIG. 3(b), temperature rise is concentrated in the overlapping region or areas. In order to prevent such overlapping, the spatial distance D (referred to as US inter-beam distance D) between the neighboring beams B1 and B2 irradiating the focusing region F is adjustable. Thus, the shear elasticity measurement can be made for a sufficiently long period of time as required. By controlling the transmission aperture of the device, that is, by moving the aperture in the scanning direction, a US beam can be irradiated to a plurality of focusing regions F.

The control circuit 8 calculates the positions in the biological object to which a US beam is transmitted in accordance with a given region of shear elasticity measurement, and controls the orientations of the transmitting US beam by informing the ultrasound transmitter circuit 4 of the positions. Consequently, it is possible for the probe 3 to irradiate a plurality of focusing regions F by adjusting the inter-beam distance D between two neighboring beams. The shear elasticity measurement domain, in which the shear elasticity is measured, can be set up by the examiner by inputting in the shear-elasticity property measurement-indication unit 11 such information as the width and depth of the area. In the case where the three-dimensional shear elasticity measurement is performed, depth information is further input. In this manner, as the shear elasticity measurement domain is set up, the control circuit 8 simulates an expected temperature rise in the physiological domain and sets the magnitude of the inter-beam distance D based on the information used to set up the shear elasticity measurement domain. The inter-beam distance D is set so that multiple ultrasound wave propagation areas will not superimpose one another.

As described above, the ultrasound diagnostic device of the present invention provides an apparatus configured to measure the shear elasticity of an object irradiated by an ultrasound wave emitted from the probe 3, which is adapted to irradiate multiple focusing regions with the wave and is equipped with a calculation circuit (calculation unit) 10.

The probe 3 can adjust the inter-beam distance D of the US beams to be irradiated to the multiple focusing regions. In this arrangement, in irradiating a plurality of focusing regions, US beams are spaced apart by a distance D so as to disperse temperature rise in the physiological object.

If the distance D is not sufficiently large, the temperature rise in a certain area (especially in the focusing region F) as shown in FIG. 3(b) irradiated by overlapping beams B1 and B2, for example, may exceed the predetermined threshold and/or the predetermined range, although it is not the case in those domains where beams B1 and B2 do not overlap. In such an instance as stated above, the control circuit 8 determines the inter-beam distance D between the beams B1 and B2 so that the beams will not overlap anywhere in the biological object and the temperature of the object is suppressed below a maximum of 41° C., as shown in FIG. 3(c). It is noted that the control circuit 8 is capable of presetting the inter-beam distance D (for example, 3 cm) not to overlap the beam B1 with beam B2. The examiner may set an arbitrary inter-beam distance D within a given permissible range (for example, between 3 and 5 cm) via the control circuit 8.

The ultrasound diagnostic device 1 of the invention ensures the safety of a biological object irradiated with ultrasound wave by regulating the inter-beam distance D of the ultrasound wave to be irradiated to a plurality of focusing regions F while depositing ultrasound energy to the object within a predetermined temperature range.

A plurality of beams, B1 and B2, emitted from the probe 3 may be irradiated to a plurality of focusing regions F such that the focusing region F are allocated in substantially parallel to each other. FIG. 4 illustrates propagation areas of transverse ultrasound waves. In a generally known scanning scheme, a beam of ultrasound wave scans a fan-shaped area. In this scanning scheme, the direction P of propagation of the transverse US wave used in shear elasticity measurement is perpendicular to the longitudinal direction of the US wave irradiated to the fan-shaped area, as shown in FIG. 4(a).

In this case, area A of propagation of the transverse US wave (the area hereinafter referred to as a propagation area A) is a rectangular area centered at a focusing region F, as shown in FIG. 4(b). Consequently, when the US beam scans a fan-shape area, the propagation area A is oblique with respect to the direction of the probe 3 in abutment against the biological tissue. Therefore, such scanning leaves a certain portion of the measurement domain E not covered with oblique propagation areas. Thus, in order to cover the entire shear elasticity measurement domain E with oblique propagation areas A, the US beam must be irradiated more than once. In this case, overlapping of propagation areas A is inevitable in certain areas (the area hereinafter referred to as overlapping areas C), where an excessive temperature rise may takes place. It is noted that in each of the oblique propagation areas A the direction P of propagation of the transverse ultrasound wave is not parallel to the direction of the muscular tissues, thereby lowering the frame rate of the shear elasticity measurement and hence impairing the real time feature of the measurement.

FIG. 4(c) illustrates a way how overlapping areas C can be reduced by allocating a plurality of parallel focusing regions F. By having the ultrasound transmitter circuit 4 controlled by the control circuit 8 so as to cover the entire shear elasticity measurement domain E as set up by the shear-elasticity property measurement-indication unit 11, the US beams B1 and B2 may be irradiated to the surface of the biological object in the direction perpendicular thereto so that the transverse ultrasound wave propagates in substantially the direction of the muscular tissues. With such substantially parallel US beams directed to a plurality of almost parallel focusing regions, the shear elasticity measurement domain E is effectively covered by the propagation areas A. Thus, the ultrasound wave energy is deposited to the biological object, preventing superfluous irradiation of ultrasound wave that can cause unnecessary temperature rise in the biological object and help safely retain the temperature rise within a predetermined safe temperature range. It should be appreciated that the inter-beam distance D can be adjusted so as to establish the propagation areas A to cover the entire shear elasticity measurement domain E without any over lapping of the propagation areas A, thereby suppressing the energy deposition to the biological object.

As described above, in measuring the shear elasticity of a biological object, the inventive ultrasound diagnostic device is capable of adjusting the inter-beam distance D such that the propagation areas A do not overlap each other and effectively cover the entire measuring domains while suppressing the energy deposition to the biological object.

It should be noted that the probe 3 of the inventive ultrasound diagnostic device is capable of irradiating a plurality of focusing areas allocated in substantially parallel relationship without overlapping. In this scheme, substantially parallel US beams are emitted onto the substantially parallel focusing regions, so that the propagation areas efficiently cover the shear elasticity measurement domain while suppressing the ultrasound wave energy deposition to the biological object.

Alternatively, focusing regions may be switched from one to another in accordance with the framing of the frame for forming a shear elasticity measurement image. For example, in a first frame, two US beams are irradiated onto two substantially parallel non-overlapping propagation areas A for irradiation of two substantially parallel non-overlapping focusing regions F1 and F2, as shown in FIG. 5. On the other hand, in a second frame, three US beams are irradiated onto three non-overlapping propagation areas A for irradiation of three almost parallel focusing regions F3, F4, and F5. In this way, since the focusing regions F1 and F2 associated with the first frame are completely offset from the focusing regions F3, F4, and F5 associated with the second frame, it is possible to avoid a temperature rise in the biological tissue from taking place in a particular focusing region or regions (for example, focusing regions F1 and F2).

Consequently, a long time measurement of shear elasticity is permitted by properly regulating the distribution of the temperature rise in the biological object. Furthermore, the frame rate of the shear elasticity measurement is improved in this scheme.

As described above, the probe 3 of the inventive ultrasound diagnostic device is adapted to irradiate a plurality of focusing regions each specified by one specific frame that defines a particular focusing region to be imaged, wherein the positions of the focusing regions to be imaged may be switched by switching the frames in sequence from one to another. In this configuration, by selectively irradiating different focusing regions in sequence selected by a frame, concentration of temperature rise in a certain focusing region is avoided. That is, a profile of temperature rise distribution is properly regulated.

Third Embodiment

Figure 6:
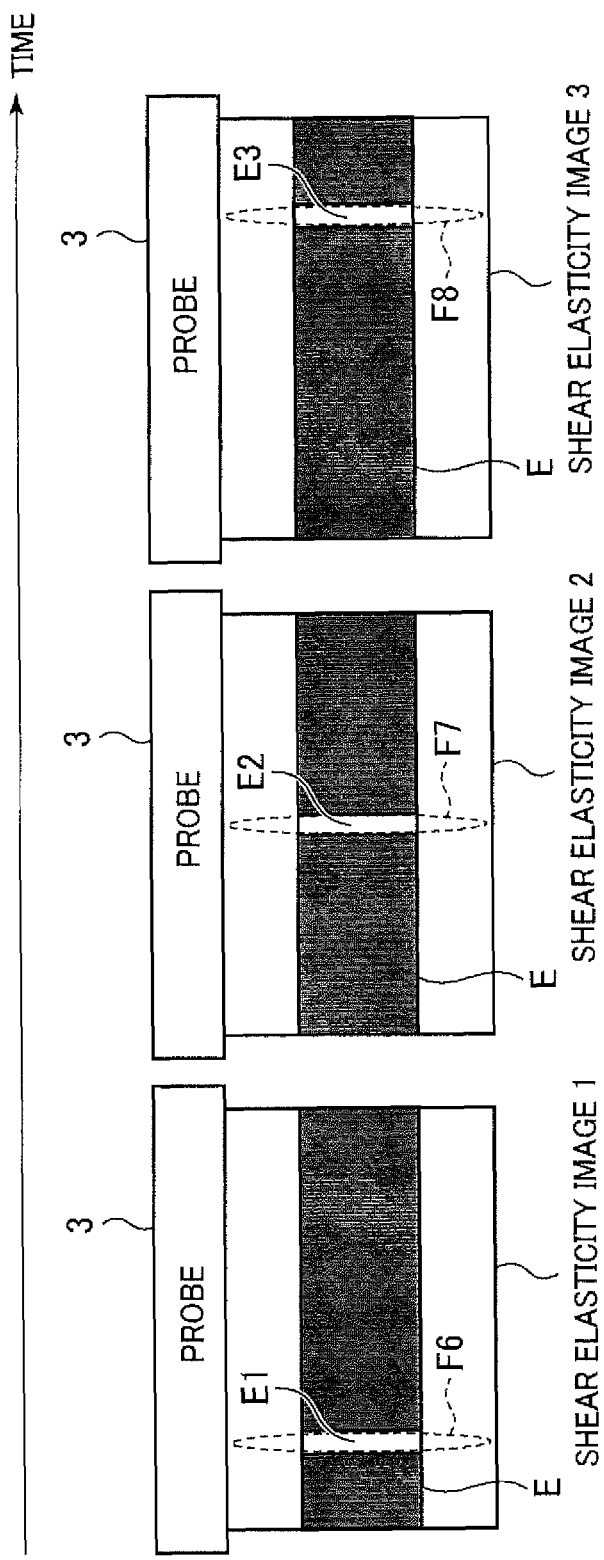
FIG. 6 briefly shows images obtained in a shear elasticity measurement by the ultrasound diagnostic device in accordance with a third embodiment of the invention.

Referring to FIG. 6, there is shown an ultrasound diagnostic device in accordance with a third embodiment of the invention. Features of the third embodiment are the same as those of the first and second embodiments unless otherwise stated. FIG. 6 is an overview of shear elasticity images obtained by the ultrasound diagnostic device in accordance with the third embodiment. The control circuit 8 determines whether or not the shear elasticity calculation is needed for the focusing regions F6-F8 based on at least one of the biological displacements caused by longitudinal ultrasound wave and transverse ultrasound wave in the focusing regions F6-F8. If the control circuit 8 determines that the shear elasticity need not be calculated for the focusing regions F6-F8, the calculation circuit 10 calculates shear elasticity in the measurement domain E other than the focusing regions F6-F8, excluding those measurement domains E1-E3 that belong to the focusing regions F6-F8.

As described above, the control unit (control circuit 8) of the inventive ultrasound diagnostic device is adapted to determine whether or not the shear elasticity of a particular focusing region needs to be calculated based on at least one of biological displacements caused in that focusing region by the longitudinal and transverse ultrasound waves. In this scheme, an instruction is established not to perform shear elasticity calculation for those biological domains that are expected to exhibit a large biological displacement caused by a longitudinal ultrasound wave, or little biological displacement caused by a transverse ultrasound wave. Omission of unnecessary shear elasticity calculation for the focusing region helps avoid unwanted temperature rise in these domains, thereby permitting suppression of the biological temperature rise in the domains within a predetermined safe range.

In order to generate a transverse ultrasound wave for the measurement of the shear elasticity of a biological tissue of interest, it is necessary to compress a certain volume of the biological tissue with a longitudinal ultrasound wave. As a result, longitudinal expansions and contractions of the biological tissue take place, resulting in a transverse wave that propagates in the biological tissue in the transverse directions. If the compressed/expanded volume occupies an infinitely small area, there can be no region in the biological tissue where a longitudinal wave is dominant. However, any actual biological tissue occupies a finite area that there is always a biological domain where a longitudinal ultrasound wave is dominant. As an example, the width of a US beam of −20 dB is in the range from about 0.3 to 2.0 mm, although the width varies with such parameters as the probe configuration, and the frequency, waveform, and power of the ultrasound wave transmitted. In a focusing region under such US beam, dominant displacement of a biological tissue is generated (by the longitudinal ultrasound wave) mainly in the direction of the irradiating US beam, and little transverse displacement (caused by the transverse ultrasound wave) is observed in the direction perpendicular to the direction of the ultrasound beam. This may result in errors in the information on the shear elasticity measurement.

In the present embodiment, the control circuit 8 constructs a simulated profile of an US beam emitted for an shear elasticity measurement based on the information inputted from the shear-elasticity property measurement-indication unit 11 regarding the shear elasticity measurement domains, the configuration of the probe 3, the frequency, waveform, and transmission power of the ultrasound wave used. The control circuit 8 also determines those biological portions expected to exhibit a large displacement caused by a longitudinal ultrasound wave (exceeding a predetermined threshold) and those biological portions expected to generate a little transverse displacement (below a predetermined threshold) caused by the transverse ultrasound wave. The control circuit 8 then instructs the calculation circuit 10 not to calculate the shear elasticity of a focusing region in that portion of the large displacement caused by the longitudinal ultrasound, and in the portion where only a little transverse wave is generated, and instructs the digital scanning converter (DSC) 6 not to display the result of the shear elasticity measurements in the focusing region.

In the course of time, a plurality of shear elasticity images 1-3 are constructed as shown in FIG. 6. In connection with the shear elasticity image 1 (referred to as first image), the control circuit 8 determines whether or not the shear elasticity be calculated for the focusing region F6 based on the simulated profile of at least one of the displacement caused by the longitudinal ultrasound wave and the displacement caused by the transverse ultrasound wave in the focusing region F6 caused by a longitudinal ultrasound wave. In the case where the control circuit 8 has determined not to calculate the shear elasticity for the focusing region F6, the calculation circuit 10 does not calculate the shear elasticity of the shear elasticity measurement domain E1 in the focusing region F6, but calculates shear elasticity of a measurement domain E not in the measurement domain E1. Similarly, in connection with the shear elasticity images 2 and 3, the calculation circuit 10 calculates the shear elasticity in the shear elasticity measurement domain E excluding the focusing regions F7 and F8, but does not calculate shear elasticity in the shear elasticity measurement domains E2 and E3 lying in the regions F7 and F8.

In this way, when a determination is made not to calculate the shear elasticity of a first focusing region, the calculation circuit 10 calculates the shear elasticity of the first focusing region based on the shear elasticity induced in the second focusing region (other than the first focusing region) by the ultrasound wave irradiated thereto. In this configuration, if shear elasticity calculation is not performed for a focusing region (referred to as missing region), complete shear elasticity measurement information of the entire se measurement domains can be obtained, since the shear elasticity of the missing region can be calculated from the shear elasticity of other focusing regions, In this mode, an instruction is made by the control circuit 8 not to display the shear elasticity of a biological tissue that exhibits unreasonably large displacement caused by a longitudinal ultrasound wave and the shear elasticity of a domain in which generation of a transverse ultrasound wave is less likely. As a result, unreasonable or erroneous shear elasticity information will not be displayed. Consequently, the ultrasound diagnostic device can provide optimum diagnostic information and reduce erroneous diagnoses. By omitting shear elasticity calculation for a certain focusing region, it is possible to avoid unnecessary temperature rise in that domain and safely keep the temperature rise in the biological object within a predetermined temperature range.

In this mode, when the control circuit 8 has determined not to calculate the shear elasticity for a focusing region F, the calculation circuit 10 does not calculate the shear elasticity of the shear elasticity measurement domain E in the focusing region F, but calculates the shear elasticity of the measurement domain E not in the focusing region F. Consequently, this determination gives rise a shear elasticity measurement domain E1 for which shear elasticity is not calculated, as seen, for example, in the shear elasticity image 1. In this case, the calculation circuit 10 calculates the shear elasticity for the focusing region F6 from the shear elasticity induced in other focusing regions F7 and F8 (shown in images 2 and 3) by the ultrasound wave irradiated thereto, not from the shear elasticity induced in the domain F6 of the shear elasticity image 1. The monitor 7 displays the first shear elasticity image 1 superimposed with a second image calculated on the basis of the shear elasticity induced in the focusing regions F7 and F8 (other than F6) by ultrasound wave.

Figure 7:
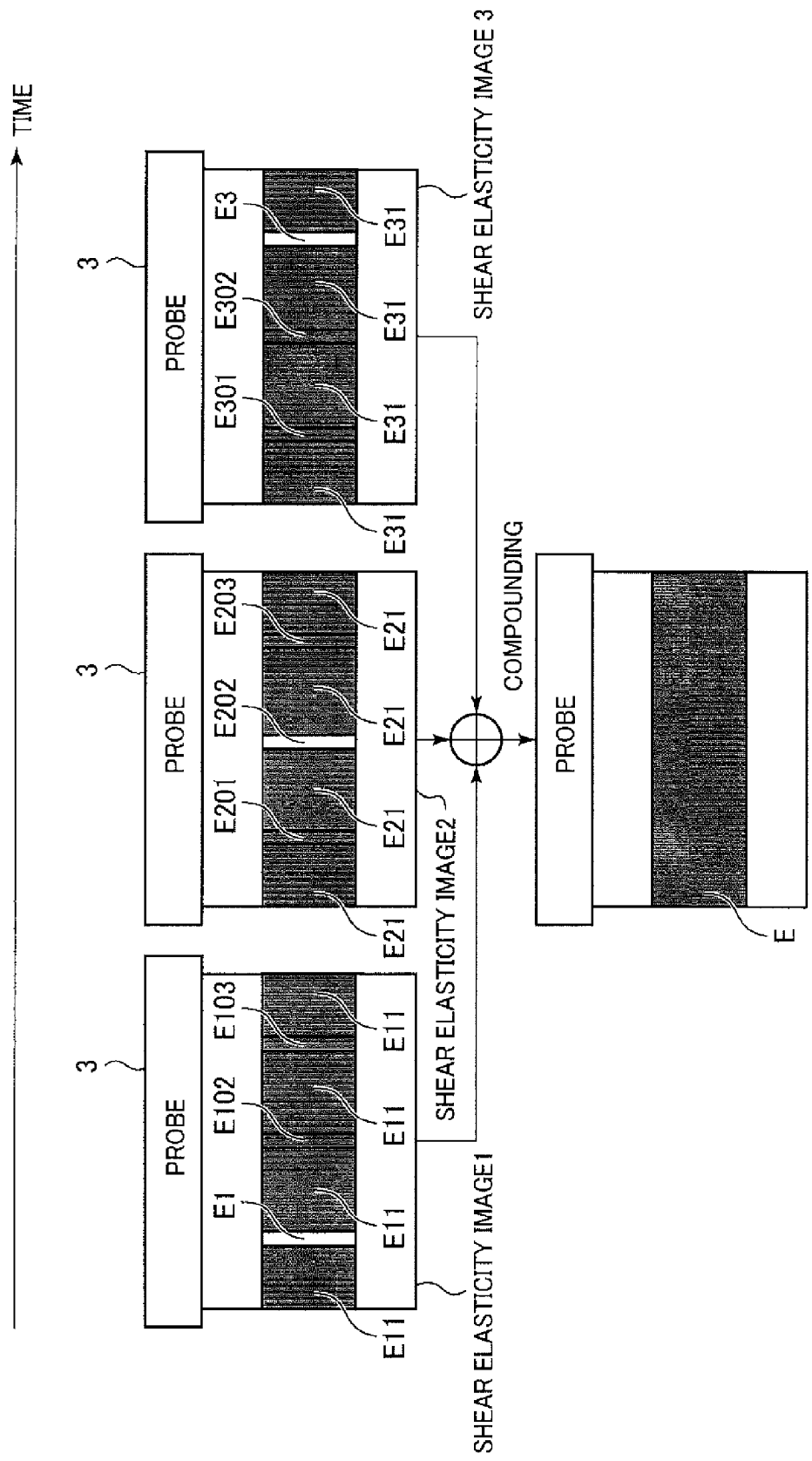
FIG. 7 shows how a plurality of shear elasticity images are superimposed.

FIG. 7 illustrates how a plurality of shear elasticity images are superimposed. As seen in FIG. 7, there appear in the shear elasticity images 1-3 some 'missing regions' E1-E3 say, where shear elasticity is not calculated. On the other hand, the shear-elasticity space compound circuit 12 can complement the shear elasticity for the missing regions E1-E3 by superimposing the shear elasticity images 1-3. Thus, the shear elasticity image for the entire shear elasticity measurement domain E can be obtained.

In compounding the shear elasticity images 1-3, the shear-elasticity property measurement-indication unit 11 sets up a compounding ratio of these images based on such parameters as the capture rate of each shear elasticity image and the positions of the missing regions in the respective images. For example, the compounding ratio of the missing region E1 of the shear elasticity image 1 is set to 0 while the compounding ratios of the domains E201 and E301 of the shear elasticity images 2 and 3, respectively, associated with the missing region E1, are set to 0.5 and 0.5, respectively. In this instance, therefore, the compounding ratio of the respective domains E1, E201, and E301 associated with the missing region E1 is given by the following formula.

$$(E1:E201:E301)=(0:0.5:0.5) \qquad (3)$$

The sum of the compounding ratios equals 1. Since the compounding ratio of the domain E1 is 0, an arbitrary compound ratios can be set to the domains E201 and E301. For example, the compound ratio of the domains E1, E201, and E301 may be set to $$(E1:E201:E301)=(0:0.25:0.75) \qquad (4)$$

On the other hand, the compound ratios of the domains E11, E21, and E31 having no missing regions, that is, the compound ratios of the domains in the respective images free of the missing regions E1, E2, and E3, and free of domains E102, E103, E201, E203, E301, and E302 (associated with the missing regions E1, E2, and E3), can be set to an arbitrary ratio, provided that the sum of their compounding ratios equals 1. For example, the compound ratio of the domains E11, E21, and E31 may be set to $$(E11:E21:E31)=(0.2:0.6:0.2) \qquad (5)$$

As shown in FIG. 7, the shear-elasticity space compound circuit 12 superimposes the shear elasticity images 1-3 by weighting with the compound ratio.

In this mode of the invention, a decision made by the control circuit 8 that the shear elasticity of a focusing region F is not made will result in missing regions E1, E2, and E3. Nevertheless, complete diagnostic information on the focusing region F can be obtained by complementing missing shear elasticity information of the missing region E1-E3, so that a shear elasticity image is secured that provides complete information necessary for the diagnosis of the disorder.

As described above, the inventive ultrasound diagnostic device displays on the display 7 the first shear elasticity image of a first focusing region for which shear elasticity is not directly calculated, superimposed with a second shear elasticity image which contains its shear elasticity is calculated based on the effect of ultrasound radiation irradiated to a second focusing region other than the first. In this scheme, if the shear elasticity image of a domain has a missing region, it is possible to supplement missing shear elasticity information for the missing region to construct a complete shear elasticity image of the domain.

The present invention has been described with reference to the foregoing embodiments, which embodiments are intended to be illustrative of the present inventive concepts rather than limiting. Rather, variations and modifications of the present invention can be effected within the scope of the invention.

INDUSTRIAL UTILITY OF THE INVENTION

The inventive ultrasound diagnostic device can draw attention of an examiner of the ultrasound diagnostic device by displaying information on the temperature rise in a physiological object, thereby enabling him to perform shear elasticity measurement of a biological tissue of the object under ultrasound radiation while safely retaining the temperature of the biological object within a predetermined range.

BRIEF DESCRIPTION OF SYMBOLS 1 ultrasound diagnostic device
2 object
3 probe
4 ultrasound transmitter circuit
5 ultrasound receiving circuit
6 digital scanning converter (DSC)
7 monitor
8 control circuit
9 operational panel
10 calculation circuit
11 shear-elasticity property measurement-indication unit
12 shear-elasticity space compound circuit

The invention claimed is:

1. An ultrasound diagnostic device, the ultrasound diagnostic device comprising:
a control unit that is implemented by a processor; and
a calculation unit that is implemented via the control unit and that is configured to calculate a shear elasticity of an object, wherein the ultrasound diagnostic device measures the shear elasticity of the object by an ultrasound wave from a probe, wherein the probe irradiates an ultrasound wave to a plurality of focusing regions of the object; and
wherein
the control unit constructs a simulated profile of an ultrasound beam based on at least one of a shape of the probe, and a transmission frequency, a transmission waveform and a transmission power of the ultrasound wave,
when the control unit determines, using the simulated profile, that a displacement of tissue of the object in a first focusing region of the plurality of focusing regions is larger than a predetermined threshold due to a longitudinal ultrasound wave and/or a displacement of the tissue in the first focusing region is smaller than a predetermined threshold due to a transverse ultrasound wave,
the control unit controls the calculation unit to calculate the shear elasticity of the first focusing region based on another ultrasound wave irradiated to a second focusing region of the plurality of focusing regions other than the first focusing region instead of an ultrasound wave irradiated to the first focusing region.

2. The ultrasound diagnostic device according to claim 1, wherein a spatial distance between beams of the ultrasound wave emitted to the focusing regions is adjustable.

3. The ultrasound diagnostic device according to claim 2, wherein the spatial distance is adjustable in responding to a propagation area of the ultrasound wave for measuring the shear elasticity.

4. The ultrasound diagnostic device according to claim 2, wherein a plurality of propagation areas are set up not to overlap each other.

5. The ultrasound diagnostic device according to claim 1, wherein a plurality of focusing regions are allocated in parallel to each other.

6. The ultrasound diagnostic device according to claim 1, wherein positions of the plurality of focusing regions are switched in accordance with an imaging frame that establishes an image of the shear elasticity.

7. The ultrasound diagnostic device according to claim 1, further comprising:
a display configured to display a shear elasticity image, wherein when the control unit determines not to calculate the shear elasticity of a first focusing region, the display superimpose the first shear elasticity image where the shear elasticity is not calculated with a second shear elasticity image generated from the shear elasticity by the ultrasound wave irradiating the second focusing region.

* * * * *